United States Patent [19]

Choi et al.

[11] Patent Number: 6,127,412

[45] Date of Patent: *Oct. 3, 2000

[54] HALOGEN SUBSTITUTED CARBAMATE COMPOUNDS FROM 2-PHENYL-1,2-ETHANEDIOL

[75] Inventors: Yong Moon Choi, Towaco; Min Woo Kim, Montvale; Jeonghan Park, Flanders, all of N.J.

[73] Assignee: SK Corporation, Fairfield, N.J.

[*] Notice: This patent is subject to a terminal disclaimer.

[21] Appl. No.: 09/349,852

[22] Filed: Jul. 8, 1999

Related U.S. Application Data

[60] Continuation of application No. 09/220,494, Dec. 23, 1998, which is a division of application No. 08/781,101, Jan. 9, 1997, Pat. No. 5,854,283, which is a continuation-in-part of application No. 08/586,497, Jan. 16, 1996, Pat. No. 5,698,588.

[51] Int. Cl.$^7$ ....................................... A61K 31/27
[52] U.S. Cl. ................................. 514/483; 560/164
[58] Field of Search ........................ 560/164; 514/483

[56] References Cited

U.S. PATENT DOCUMENTS

| | | | |
|---|---|---|---|
| 3,265,728 | 8/1966 | Bossinger | 560/164 |
| 3,313,692 | 4/1967 | Bossinger | 560/164 |
| 5,698,588 | 12/1997 | Choi | 560/164 |
| 5,854,283 | 12/1998 | Choi | 560/164 |

*Primary Examiner*—Michael L. Shippen
*Attorney, Agent, or Firm*—Gibbons, Del Deo, Dolan, Griffinger & Vecchione

[57] ABSTRACT

The optically pure forms of monocarbamates of halogenated 2-phenyl-1,2-ethanediol and dicarbamates of 2-phenyl-1,2-ethanediol have been found to be effective in the treatment of disorders of the central nervous system, especially as anti-convulsive or anti-epileptic agents.

17 Claims, No Drawings

HALOGEN SUBSTITUTED CARBAMATE COMPOUNDS FROM 2-PHENYL-1,2-ETHANEDIOL

CROSS REFERENCE TO RELATED APPLICATIONS

This is a continuation of U.S. Ser. No. 09/220,494, filed Dec. 23, 1998, pending which is a divisional of U.S. Ser. No. 08/781,101 filed Jan. 9, 1997, now U.S. Pat. No. 5,854,283, issued Dec. 29, 1998, which is a continuation-in-part of U.S. Ser. No. 08/586,497, filed Jan. 16, 1996, now U.S. Pat. No. 5,698,588, issued Dec. 16, 1997.

FIELD OF THE INVENTION

The present invention relates to novel pharmaceutically useful organic compounds and more particularly, to chemically pure compounds of mono carbamates and dicarbamates of halogen substituted 2-phenyl-1,2-ethanediol represented by the structural formula (I) and (II), wherein one enantiomer predominates and wherein the phenyl ring is substituted at X with one to five halogen atoms selected from fluorine, chlorine, bromine or iodine atoms, and wherein $R_1$, $R_2$, $R_3$, $R_4$, $R_5$ and $R_6$ are each selected from hydrogen and straight or branched alkyl groups with one to four carbons optionally substituted with a phenyl group with substituents selected from the group consisting of hydrogen, halogen, alkyl, alkyloxy, amino, nitro and cyano. The aforementioned compounds have been found to be effective in the treatment of central nervous system disorders, especially as anticonvulsants, antiepileptics, neuroprotective agents and muscle relaxants.

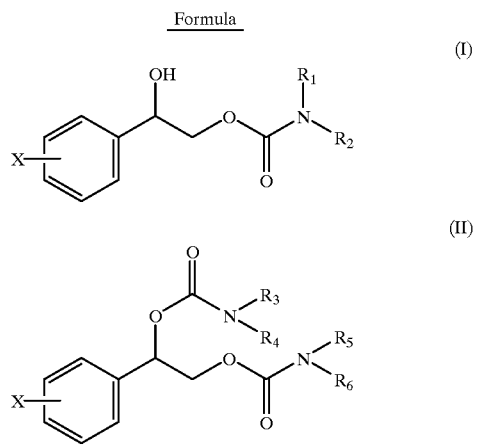

Formula (I)

Formula (II)

BACKGROUND

Racemic carbamate compounds of aryl alkyl alcohols have been known to be useful as antiepileptics and as muscle relaxants. It was reported in Toxicol. and Appl. Pharm. 2, 397–402 (1960) that when X and R are all hydrogen atoms in structural formula (I), the compound is effective as an antiepileptic agent. Dicarbamate compounds of 2-methyl-3-propyl-1,3-propanediol has been reported and their pharmacological effects have been described in J. Pharmacol. Exp. Ther., 104, 229 (1952).

In U.S. Pat. No. 3,265,728, racemic carbamate compounds represented by the structural formula (III) with a substituent on the phenyl ring has been disclosed as useful in treating central nervous system disorders. In the structural formula (III), $R_7$ is carbamate or methylene carbamate, $R_8$ is alkyl with 1–2 carbons, hydroxyalkyl with 1–2 carbons, hydroxy or hydrogen, $R_9$ is hydrogen, alkyl with 1–2 carbons and Y is selected from the group consisting of fluorine, chlorine, bromine, iodine, methyl, methoxy, phenyl, nitro or amine groups.

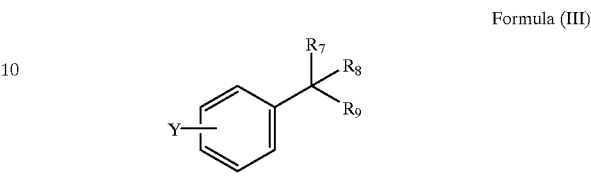

Formula (III)

In U.S. Pat. No. 3,131,692, the racemic carbamate compounds represented by the Formula (VI) have been disclosed as agents for improved central nervous system treatment with substantially reduced cholinergic side effects. In structural formula (VI), W represents an aliphatic radical containing less than 4 carbon atoms, wherein $R_{10}$ represents an aromatic radical, $R_{11}$ represents hydrogen or an alkyl radical containing less than 4 carbon atoms, and Z represents hydrogen or hydroxy or alkoxy and alkyl radicals containing less than 4 carbon atoms or the radical —OC(=O)B, in which B represents an organic amine radical of the group consisting of heterocyclic, ureido and hydrazino radicals and the radical —N($R_{12}$)$_2$ wherein $R_{12}$ represents hydrogen or an alkyl group containing less than 4 carbon atoms. Moreover, at least one Z in the structural formula (VI) represents the radical —OC(=O)B.

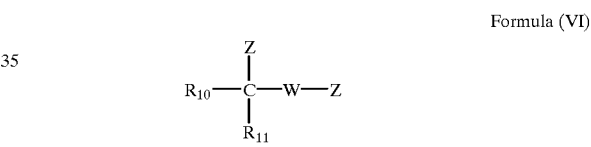

Formula (VI)

In U.S. Pat. No. 2,884,444, dicarbamate compounds from 2-phenyl-1,3-propanediol have been disclosed, and in U.S. Pat. No. 2,937,119 carbamate compounds such as isopropylmeprobamate have been disclosed.

Some of the carbamate compounds described in the previous paragraphs are currently being used in the treatment of central nervous system disorders. However exploratory research is being conducted to identify new carbamate compounds which are even more effective for use in the treatment of various central nervous system diseases.

It is a general phenomenon common to all bioactive substances that some differences are usually observed for the activities of the enantiomers when a stereogenic center is present in a bioactive molecule. Typically, by resolving a racemate mixture of bioactive compound, one enantiomer shows higher activity than the racemate while a lower activity is observed with the other enantiomer. Still one must not blindly accept the foregoing generality when developing bioactive molecules without first obtaining experimental verification, since, on occation, unexpected results are observed due to the complex nature of biological responses to foreign substances.

It is an object of the present invention to provide optically active novel carbamate compounds for therapeutic use, especially compositions containing such carbamate compounds as the active ingredient, which possess therapeutic activity in treating diseases of the central nervous system.

SUMMARY OF THE INVENTION

In order to achieve the foregoing object, as well as other objects of the present invention, the carbamate compounds represented by the structural formulas (I) and (II) have a chiral carbon on its benzylic position, hence there can be two optical enantiomers of the compounds represented by the structural formulas (I) and (II). Generally speaking, optical enantiomers of various compounds exhibit different pharmacological and toxicological activities, and it is the current trend in the pharmaceutical industry to develop one enantiomer with either fewer toxicological effects or better efficacy.

This invention discloses the carbamate compounds represented by the structural formula (I) and (II), in which one enantiomer is present predominanately. These compounds are useful in the treatment of central nervous system diseases, particularly as anticonvulsants, antiepileptics, neuroprotective agents and centrally acting muscle relaxants.

DETAILED DESCRIPTION OF THE INVENTION

This invention provides novel pharmaceutically useful optically active organic carbamate compounds represented by the structural formulas (I) and (II), wherein the phenyl ring is substituted at X with one to five halogen atoms selected from fluorine, chlorine, bromine or iodine atoms, and $R_1$, $R_2$, $R_3$, $R_4$, $R_5$ and $R_6$ is a functional group selected from hydrogen and straight or branched alkyl groups with one to four carbons optionally substituted with a phenyl group with substituents selected from the group consisting of hydrogen, halogen, alkyl, alkyloxy, amino, nitro and cyano.

Formula

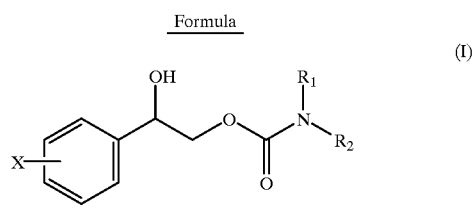

(I)

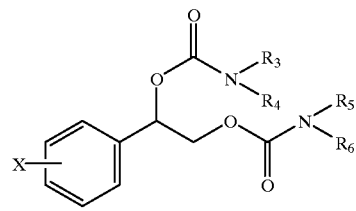

(II)

The compounds of the present invention possess selective pharmacological properties and are useful in treating and preventing central nervous system disorders including convulsions, epilepsy, stroke and muscle spasm.

It will be apparent to those skilled in the art that the compounds of the present invention contain chiral centers. The compounds of formula (I) and (II) contain an asymmetric carbon atom at the benzylic position, which is the aliphatic carbon adjacent to the phenyl ring. The therapeutic properties of the compounds may to a greater or lesser degree depend on the stereochemistry of a particular compound. The scope of the present invention includes pure enantiomeric forms and enantiomeric mixtures wherein one of the enantiomers predominates the compounds respresented by the structural formulas (I) and (II). Preferably, one of the enantiomers predominates to the extent of about 90% or greater, and most preferably, about 98% or greater.

The carbamate compounds represented by the structural formula (I) may be prepared by the synthetic method described in Scheme 1, a detailed description of which follows. A 2-phenyl-1,2-ethanediol with halogen substituent on the phenyl ring is reacted with diethylcarbonate in the presence of catalytic amount of sodium methoxide. The by-product methanol is removed by a vacuum distillation and the Scheme 1

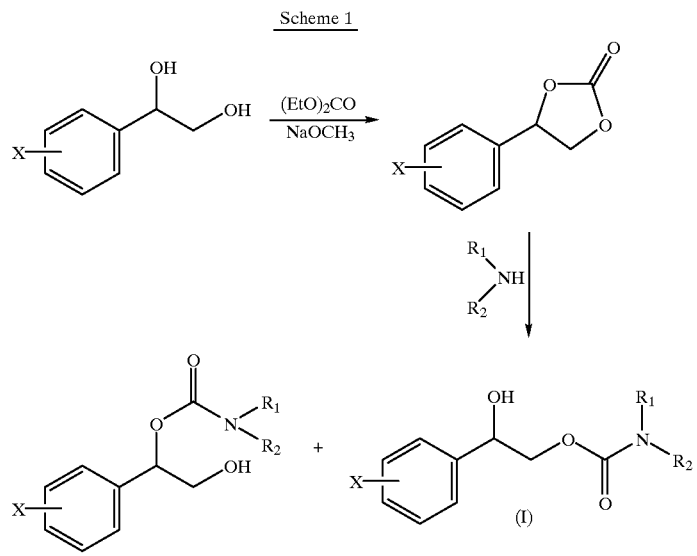

residual product is dried in vacuo. The crude reaction product is subsequently dissolved in a lower alkanol, such as methanol, and an excess amount of an amine is added to the reaction solution at room temperature to provide two regioisomeric forms of a monocarbamate of 2-phenyl-1,2-ethanediol with a halogen substituent on the phenyl ring. Regioisomeric forms of monocarbamates of 2-phenyl-1,2-ethanediol with a halogen substituent on the phenyl ring are separated by flash column chromatography providing the desired compound as the major product. In the structural formula (I) in Scheme 1, the phenyl ring is substituted at X with from one to five halogen atoms selected from fluorine, chlorine, bromine or iodine atoms, and $R_1$ and $R_2$ is a functional group selected from hydrogen and straight or branched alkyl with one to four carbons optionally substituted with phenyl group with substituents selected from a group consisting of hydrogen, halogen, alkyl, alkyloxy, amino, nitro and cyano.

The carbamate compounds represented by the structural formula (II) may be prepared by the synthetic method described either in Scheme 2, in Scheme 3 or in Scheme 4, the detailed descriptions of which follow.

When $R_3$, $R_4$, $R_5$ and $R_6$ are hydrogen, the desired dicarbamate compound is prepared by the synthetic method described in Scheme 2. A 2-phenyl-1,2-ethanediol with halogen substitutent on the phenyl ring is dissolved in a solvent selected from a group consisted of acetonitrile, tetrahydrofuran and dichloromethane, and is treated with excess sodium cyanate. The resulting mixture is cooled in an ice-bath, and excess methanesulfonic acid is added slowly. When the starting diol is not detected by thin layer chromatography, the reaction mixture is neutralized with aqueous sodium hydroxide and extracted with methylene chloride. The organic extract is dried, filtered, concentrated and the desired compound is purified by flash column chromatography.

In structural formulas (II) in Scheme 2, the phenyl ring is substituted with from one to five halogen atoms selected from fluorine, chlorine, bromine or iodine atoms.

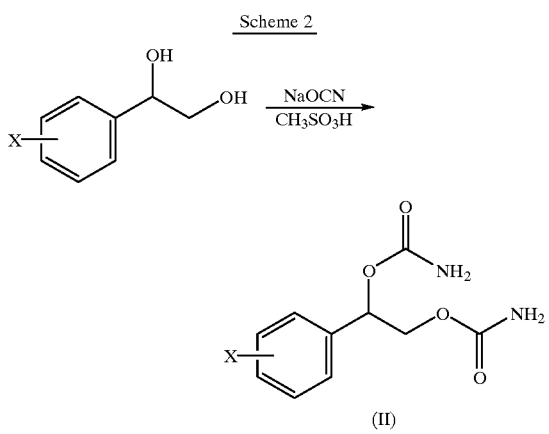

When the carbamate units in a dicarbamate represented by structural formula (II) are identical, that is when $R_3$=$R_5$ and $R_4$=$R_6$, the desired compound is prepared by synthetic method described in Scheme 3. A 2-phenyl-1,2-ethanediol with halogen substituent on the phenyl ring is dissolved in dichloromethane and is treated with about 2 equivalents of carbonyl diimidazole. The resulting mixture is stirred until the starting material is not observed by thin layer chroma-tography analysis, and the mixture is treated with excess amount of amine ($R_3R_4NH$). It takes typically more than 24 hours to complete the reaction. After a routine aqueous wash, the crude reaction product is purified by flash column chromatography to provide the desired product.

In structural formula (II) in Scheme 3, the phenyl ring is substituted at X with from one to five halogen atoms selected from fluorine, chlorine, bromine or iodine atoms, and $R_3$ an $R_4$ may be a functional group selected from hydrogen and straight or branched alkyl with one to four carbons optionally substituted with a phenyl group with substituents selected from the group consisting of hydrogen, halogen, alkyl, alkyloxy, amino, nitro and cyano.

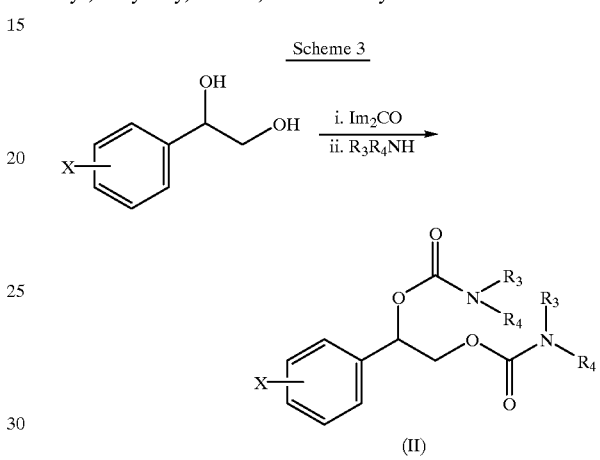

When the carbamate units in a dicarbamate represented by the structural formula (II) are different, the desired compound is prepared from a corresponding monocarbamate represented by the structural formula (I) which was prepared by the synthetic method described in Scheme 1, using the synthetic method described in Scheme 4. A 2-phenyl-1,2-ethanediol monocarbamate from a group of compounds represented by the structural formula (I) is treated with about 1 equivalent of carbonyl diimidazole. The resulting mixture is stirred until the starting material is not observed by thin layer chromatography analysis, and the mixture is treated with an excess amount of amine ($R_5R_6NH$). It takes typically more than 24 hours to complete the reaction. After a routine aqueous wash, the crude reaction product is purified by flash column chromatography to provide the desired product.

In structural formulas (II) in Scheme 4, the phenyl ring is substituted at X with from one to five halogen atoms selected from fluorine, chlorine, bromine or iodine atoms, and $R_3$, $R_4$, $R_5$ and $R_6$ is a functional group selected from hydrogen and straight or branched alkyl with one to four carbons optionally substituted with phenyl group with substituents selected from the group consisting of hydrogen, halogen, alkyl, alkyloxy, amino, nitro and cyano.

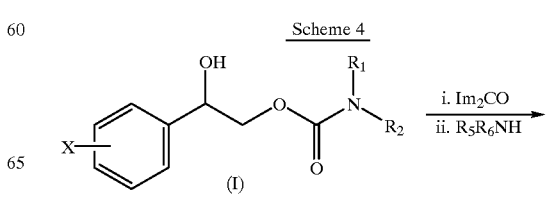

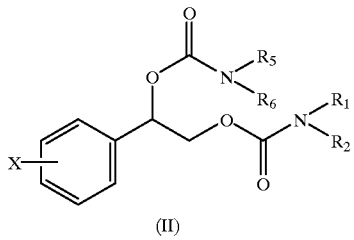

(II)

In utilizing the compounds of the present invention for the treatment of diseases of the central nervous system, particularly the treatment of convulsions, epilepsy, stroke and muscle spasm, it is preferred to administer the compounds orally. Since the compounds are well absorbed orally, it usually will not be necessary to resort to parenteral administration. For oral administration, the present carbamate compounds are preferably combined with a pharmaceutical carrier. The ratio of the carrier to the compounds of the present invention is not critical to achieve the effects of the medicine on the central nervous system, and they can vary considerably, depending on whether the composition is to be filled into capsules or formed into tablets. In tableting, it is usually desirable to employ at least as much pharmaceutical carrier as the pharmaceutically active ingredients. Various edible pharmaceutical carriers or mixtures thereof can be used. Suitable carriers, for example, are a mixture of lactose, dibasic calcium phosphate and corn starch. Other pharmaceutically acceptable ingredients can be further added, including lubricants such as magnesium stearate.

The therapeutic use of the compounds claimed in the present invention as anticonvulsants has been proven by the "Maximal ElectroShock (MES)" test, which is a well-established pharmacological screening method for anticonvulsants against partial seizures, and the results are presented in Table I.

The procedure employed in the MES test for anticonvulsants follows. The compound dosing solutions were prepared in saline, and the subject namely, mice (CF-1 strain), were dosed orally. After the designated number of hours, maximal electroshock was induced in mice via corneal electrodes using IITC Life Science model 11A Shocker at 50 mA–60 Hz for 0.2 second. Upon inducing maximal electroshock, the elimination of hindlimb tonic extension was considered as providing evidence of the protection by an anticonvulsant. Median efficacy dose (ED50) levels were determined using three different dose levels with at least 6 mice in each group. Compounds with smaller ED50 value are more potent as anticonvulsants.

TABLE I

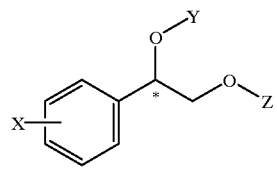

| Entry | X | * (Chirality) | Y | Z | ED50 (mg/Kg) | Hour |
|---|---|---|---|---|---|---|
| 1 | o-Cl | rac. | H | $CONH_2$ | 37.7 | 1 |
| 2 | o-Cl | R | H | $CONH_2$ | 13.0 | 1 |
| 3 | o-Cl | S | H | $CONH_2$ | 50.0 | 1 |
| 4 | 2,6-$Cl_2$ | S | H | $CONH_2$ | 9.4 | 1 |
| 5 | o-Cl | rac. | $CONH_2$ | $CONH_2$ | 25 | 1 |
| 6 | o-Cl | R | $CONH_2$ | $CONH_2$ | 16.0 | 1 |
| 7 | o-Cl | S | $CONH_2$ | $CONH_2$ | 22.0 | 1 |
| 8 | p-Cl | rac. | $CONH_2$ | $CONH_2$ | 29.1 | 1 |
| 9 | p-Cl | R | $CONH_2$ | $CONH_2$ | 26.2 | 1 |
| 10 | p-Cl | S | $CONH_2$ | $CONH_2$ | 21.5 | 4 |
| 11 | 2,6-$Cl_2$ | rac. | $CONH_2$ | $CONH_2$ | 7.4 | 1 |
| 12 | 2,6-$Cl_2$ | R | $CONH_2$ | $CONH_2$ | 10.7 | 1 |
| 13 | o-Cl | R | $CONH_2$ | $CONHCH_3$ | 8.9 | 4 |
| 14 | o-Cl | R | $CONHCH_3$ | $CONHCH_3$ | >20 | 4 |
| 15 | o-Cl | R | CONHiPr | CONHiPr | ~10 (ip) | 1 |
| 16 | o-Cl | R | CONHPh | CONHPh | >20 | 4 |
| 17 | o-Cl | R | $CONHCH_2Ph$ | $CONHCH_2Ph$ | >20 | 4 |

A better understanding of the present invention may be obtained in light of following examples which are set forth to illustrate, but are not to be construed to limit, the present invention.

The diols used in the syntheses of carbamate compounds were prepared by a dihydroxylation reaction from their corresponding styrenic compound. In preparations of optically active diols, Sharpless's asymmetric dihydroxylation catalysts were used.

EXAMPLE 1

(DL)-(2-(2-Chlorophenyl)-2-carbamoyloxyethyl) oxocarboxamide:

General procedure for preparing unsubstituted dicarbamate compounds (DL)-1-o-Chlorophenyl-1,2-ethanediol was dissolved in tetrahydrofuran (115 mL) and sodium cyanate (9.0 g) and methanesulfonic acid (9.5 mL) was added in an ice bath. The resulting reaction mixture was stirred for 18 hours, extracted with tetrahydrofuran dichloromethane mixture, washed with 5% aqueous sodium hydroxide, dried over sodium sulfate, filtered, concentrated and purified by flash column chromatography to yield a white solid. Analytically pure (DL)-(2-(2-Chlorophenyl)-2-carbamoyloxyethyl)oxocarboxamide (m.p. 190° C.) was obtained after recrystallization from ethanol-ether mixture.

EXAMPLE 2
(R)-(2-(2-Chlorophenyl)-2-carbamoyloxyethyl) oxocarboxamide (R)-(2-(2-Chlorophenyl)-2-carbamoyloxyethyl) oxocarboxamide (2.1 g, yield 46%, m.p. 172–174° C., $[\alpha]_D$=84.9 (c=2.70, DMF)) was prepared using the same synthetic method described in Example 1, except that (R)-1-o-chlorophenyl-1,2-ethanediol (3.0 g) was used instead of (D/L)-1-o-chlorophenyl-1,2-ethanediol.

EXAMPLE 3
(S)-(2-(2-Chlorophenyl)-2-carbamoyloxyethyl) oxocarboxamide (S)-(2-(2-Chlorophenyl)-2-carbamoyloxyethyl) oxocarboxamide (1.6 g, yield 35%, m.p. 167–169° C., $[\alpha]_D$=−84.1 (c=2.27, DMF)) was prepared using the same synthetic method described in Example 1, except that (S)-1-o-chlorophenyl-1,2-ethanediol was used instead of (D/L)-1-o-chlorophenyl-1,2-ethanediol.

EXAMPLE 4
(DL)-(2-(3-Chlorophenyl)-2-carbamoyloxyethyl) oxocarboxamide (DL)-(2-(3-Chlorophenyl)-2-carbamoyloxyethyl) oxocarboxamide (2.41 g, yield 80%, m.p. 188–190° C.) was prepared using the same synthetic method described in Example 1, except that (DL)-1-m-chlorophenyl-1,2-ethanediol was used instead of (DL)-1-o-chlorophenyl-1,2-ethanediol.

EXAMPLE 5
(DL)-(2-(4-Chlorophenyl)-2-carbamoyloxyethyl) oxocarboxamide (DL)-(2-(4-Chlorophenyl)-2-carbamoyloxyethyl) oxocarboxamide (1.97 g, yield 38%, m.p. 146–148° C.) was prepared using the same synthetic method described in Example 1, except that (DL)-1-p-chlorophenyl-1,2-ethanediol was used instead of (DL)-1-o-chlorophenyl-1,2-ethanediol.

EXAMPLE 6
(R)-(2-(4-Chlorophenyl)-2-carbamoyloxyethyl) oxocarboxamide (R)-(2-(4-Chlorophenyl)-2-carbamoyloxyethyl) oxocarboxamide (2.53 g, yield 84%, m.p. 178–180° C., $[\alpha]_D$=−24.38 (c=2.60, MeOH)) was prepared using the same synthetic method described in Example 1, except that (R)-1-p-chlorophenyl-1,2-ethanediol was used instead of (DL)-1-o-chlorophenyl-1,2-ethanediol.

EXAMPLE 7
(S)-(2-(4-Chlorophenyl)-2-carbamoyloxyethyl) oxocarboxamide (S)-(2-(4-Chlorophenyl)-2-carbamoyloxyethyl) oxocarboxamide (2.04 g, yield 68%, m.p. 177–179° C., $[\alpha]_D$=25.56 (c=2.75, MeOH)) was prepared using the same synthetic method described in Example 1, except that (S)-1-p-chlorophenyl-1,2-ethanediol was used instead of (DL)-1-o-chlorophenyl-1,2-ethanediol.

EXAMPLE 8
(DL)-(2-(2,6-Dichlorophenyl)-2-carbamoyloxyethyl) oxocarboxamide (DL)-(2-(2,6-Dichlorophenyl)-2-carbamoyloxyethyl) oxocarboxamide (1.71 g, yield 40%, m.p. 160–162° C.) was prepared using the same synthetic method described in Example 1, except that (DL)-1-(2,6-dichlorophenyl)-1,2-ethanediol was used instead of (DL)-1-o-chlorophenyl-1,2-ethanediol.

EXAMPLE 9
(R)-(2-(2,6-Dichlorophenyl)-2-carbamoyloxyethyl) oxocarboxamide (R)-(2-(2,6-Dichlorophenyl)-2-carbamoyloxyethyl) oxocarboxamide (7.40 g, yield 52%, m.p. °C, $[\alpha]_D$=36.01 (c=2.58, MeOH) was prepared using the same synthetic method described in Example 1, except that (R)-1-(2,6-dichlorophenyl)-1,2-ethanediol was used instead of (DL)-1-o-chlorophenyl-1,2-ethanediol.

EXAMPLE 10
(R)-(2-(2-Chlorophenyl)-2-N-methylcarbamoyloxyethyl) oxocarboxamide. General procedure for preparing mono-substituted dicarbamate compounds 1,1'-Carbonyldiimidazole (1.0 g, 6.12 mmol) was added to a solution of (R)-(2-(2-chlorophenyl-2-hydroxyethyl) oxocarboxamide (1.2 g, 5.56 mmol) in tetrahydrofuran (4 mL) at 5° C. The reaction mixture was allowed to come to room temperature and stirred 45 min. Methylamine (5.6 mL of a 2 M solution in THF) was added at 5° C. The reaction mixture was stirred for 18 hr at room temperature, extracted with ethyl acetate, washed with 0.5 aquous hydrochloric acid, saturated sodium bicarbonate and brine. The extracts were dried over sodium sulfate, filtered, concentrated and purified by flash chromatography to yield a white solid (1.4 g, yield 93%, m.p. 128–130° C., $[\alpha]_D$=0.937 (c=2.49, MeOH))

EXAMPLE 11
(R)-(2-(2-Chlorophenyl)-2-N-isopropylcarbamoyloxyethyl) oxocarboxamide (R)-(2-(2-Chlorophenyl)-2-N-isopropylcarbamoyloxyethyl)-oxocarboxamide (1.0 g, yield 62%, m.p. 163–165° C., $[\alpha]_D$=3.99 (c=2.10, MeOH) was prepared using the same synthetic method described in Example 10, except that isopropylamine was used instead of methylamine.

EXAMPLE 12
(R)-(2-(2-Chlorophenyl)-2-N-cyclopropylcarbamoyloxyethyl)oxocarboxamide (R)-(2-(2-Chlorophenyl)-2-N-cyclopropylcarbamoyloxyethyl)-oxocarboxamide (1.60, yield 96%, m.p. 111–113° C., $[\alpha]_D$=2.39 (c=2.25, MeOH) was prepared using the same synthetic method described in Example 10, except that cyclopropylamine was used instead of methylamine.

EXAMPLE 13
(R)-N-Methyl(2-(2-chlorophenyl)-2-N-methylcarbamoyloxyethyl)oxocarboxamide General procedure for preparing N,N'-disubstituted dicarbamate compounds A solution of (R)-(2-chlorophenyl)-1,2-ethanediol (2.0 g, 11.6 mmol) in tetrahydrofuran was added dropwise to a suspension of 1,1'-carbonyldiimidazole (4.13 g, 25.5 mmol) in tetrahydrofuran (10 mL) at 5° C. over a 20 min period. After stirring 1 hr at room temperature, methylamine (23.2 mL 2 M solution in THF, 46.4 mmol) was added at 5° C. After stirring 18 hr at room temperature, the reaction mixture was concentrated in vacuuo and purified by flash chromatography to give a white solid (2.03 g, 61%, m.p. 152–154)

EXAMPLE 14
(R)-N-Isopropyl(2-(2-chlorophenyl)-2-N-isopropylcarbamoyloxyethyl)oxocarboxamide (R)-N-Isopropyl(2-(2-chlorophenyl)-2-N-isopropylcarbamoyloxyethyl)oxocarboxamide (3.50 g, yield 88%, m.p. 151–153° C., $[\alpha]_D$=1.33 (c=2.63, MeOH) was prepared using the same synthetic method described in Example 13, except that isopropylamine was used instead of methylamine.

EXAMPLE 15
(R)-N-Phenyl(2-(2-chlorophenyl)-2-N-phenylcarbamoyloxyethyl)oxocarboxamide (R)-N-Phenyl(2-(2-chlorophenyl)-2-N-phenylcarbamoyloxyethyl)-oxocarboxamide (2.74 g, yield 57%, m.p. 46–48° C.) was prepared using the same synthetic method described in Example 13, except that aniline was used instead of methylamine.

EXAMPLE 16
(R)-N-Benzyl(2-(2-chlorophenyl)-2-N-benzylcarbamoyloxyethyl)oxocarboxamide (R)-N-Benzyl(2-(2-chlorophenyl)-2-N-benzylcarbamoyloxyethyl)-oxocarboxamide (2.88 g, yield 76%, m.p. 80–82° C.) was prepared using the same synthetic method described in Example 13, except that benzylamine was used instead of methylamine.

EXAMPLE 17
(DL)-(2-(2-chlorophenyl)-2-hydroxyethyl)oxocarboxamide. General procedure for preparing monocarbamate compounds In a 50 mL round bottom flask equipped with vacuum distillation apparatus, (DL)-o-chlorophenyl-1,2-ethanediol (10.98 g), diethyl carbonate (10.25 mL) and sodium methoxide (305 mg) were placed and the resulting mixture was heated in an oil bath up to 135° C. with magnetic stirring. The by-product, ethyl alcohol was collected in a receiver flask. After collecting approximately 10 mL of ethanol, the residual ethyl alcohol remaining in the reaction mixture was removed by vacuum distillation. The reaction mixture was cooled to room temperature, dissolved in dichloromethane (40 mL), washed with brine (15 mL), dried over anhydrous sodium sulfate, filtered and then concentrated in vacuo to produce (DL)-1-o-chlorophenyl-1,2-ethanediol carbonate (12.58 g, yield 100%).

In a 200 mL round bottom flask equipped with a magnetic stirrer, approximately 12 mL of liquid ammonia was condensed at −78° C., and (DL)-1-o-chlorophenyl-1,2-ethanediol carbonate (6.0 g) in methanol (200 mL) was added slowly. The reaction mixture was slowly warmed to room temperature and was stirred at room temperature for another hour, and then concentrated in vacuo. (DL)-(2-(2-Chlorophenyl)-2-hydroxyethyl)oxocarboxamide (1.97 g, yield 30%, m.p. 100° C.) was obtained after a chromatographic purification.

EXAMPLE 18
(R)-(2-(2-chlorophenyl)-2-hydroxyethyl)oxocarboxamide (R)-(2-(2-Chlorophenyl)-2-hydroxyethyl)oxocarboxamide (3.35 g, yield 45%, m.p. 133° C., $[\alpha]_D$=−63.9 (c=2.22, methanol)) was prepared using the same synthetic method described in Example 17, except that (R)-o-chlorophenyl-1,2-ethanediol was used instead of (DL)-1-o-chlorophenyl-1,2-ethanediol.

EXAMPLE 19
(S)-(2-(2-chlorophenyl)-2-hydroxyethyl)oxocarboxamide (S)-(2-(2-Chlorophenyl)-2-hydroxyethyl)oxocarboxamide (3.89 g, yield 52%, m.p. 133° C., $[\alpha]_D$=64.9 (c=2.69, methanol)) was prepared using the same synthetic method described in Example 17, except that (S)-o-chlorophenyl-1,2-ethanediol was used instead of (DL)-1-o-chlorophenyl-1,2-ethanediol.

EXAMPLE 20
(DL)-(2-3-Chlorophenyl)-2-hydroxyethyl)oxocarboxamide (DL)-1-m-Chlorophenyl-1,2-ethanediol carbonate was prepared using the same synthetic method described in Example 17, except that (DL)-1-m-chlorophenyl-1,2-ethanediol was used instead of (DL)-2-o-chlorophenyl-1,2-ethanediol in a quantitative yield.

In a 250 mL round bottom flask equipped with a magnetic stirrer, (DL)-1-m-chlorophenyl-1,2-ethanediol carbonate (10.95 g) was dissolved in methanol (60 mL) and the mixture was cooled in an ice bath. Ammonium hydroxide (30 mL, 28–30%) was added to the mixture and the mixture was stirred at room temperature for 1 hour or until the reaction was completed as evidenced by thin layer chromatography. Excess ammonium hydroxide and methanol were removed in vacuo to yield a white solid. (DL)-(2-(3-Chlorophenyl)-2-hydroxyethyl)oxocarboxamide (1.25 g, yield 10%, m.p. 90° C.) was purified by flash column chromatography.

EXAMPLE 21
(R)-(2-(3-Chlorophenyl)-2-hydroxyethyl)oxocarboxamide (R)-(2-(3-Chlorophenyl)-2-carbamoyloxyethyl)oxocarboxamide (1.77 g, 45%, m.p. 114–116° C.) was prepared using the same synthetic method described in Example 20, except (R)-1-m-chlorophenyl-1,2-ethanediol was used instead of (DL)-1-m-chlorophenyl-1,2-ethanediol.

EXAMPLE 22
(S)-(2-(3-Chlorophenyl)-2-hydroxyethyl)oxocarboxamide (S)-(2-(3-Chlorophenyl)-2-carbamoyloxyethyl)oxocarboxamide (1.36 g, yield 25%, m.p. 117–119° C., $[\alpha]_D$=12.88 (c=2.30, MeOH) was prepared using the same synthetic method described in Example 20, except (S)-1-m-chlorophenyl-1,2-ethanediol was used instead of (DL)-1-m-chlorophenyl-1,2-ethanediol.

EXAMPLE 23
(R)-(2-(4-Chlorophenyl)-2-hydroxyethyl)oxocarboxamide (R)-(2-(4-Chlorophenyl)-2-hydroxyethyl)oxocarboxamide (1.15 g, yield 31%, m.p. 110–112° C.) was prepared using the same synthetic method described in Example 24, except (R)-1-p-chlorophenyl-1,2-ethanediol was used instead of (DL)-1-m-chlorophenyl-1,2-ethanediol.

EXAMPLE 24
(S)-(2-(4-Chlorophenyl)-2-hydroxyethyl)oxocarboxamide (S)-(2-(4-Chlorophenyl)-2-hydroxyethyl)oxocarboxamide (1.14 g, yield 30%, m.p. 110–112° C., $[\alpha]_D$=18.62 (c=2.40, MeOH) was prepared using the same synthetic method described in Example 20, except (S)-1-p-chlorophenyl-1,2-ethanediol was used instead of (DL)-1-m-chlorophenyl-1,2-ethanediol.

EXAMPLE 25
(DL)-(2-(2,6-dichlorophenyl)-2-hydroxyethyl)oxocarboxamide (DL)-(2-(2,6-dichlorophenyl)-2-hydroxyethyl)oxocarboxamide (1.05 g, yield 43%, m.p. 120–122° C.) was prepared using the same synthetic method described in Example 20, except (DL)-2-(2,6-dichlorophenyl-1,2, ethanediol was used instead of (DL)-1-m-chlorophenyl-1,2-ethanediol

What is claimed is:

1. A compound comprising pure enantiomeric forms, as well as enantiomeric mixtures, of (2-(2-chlorophenyl)-2-carbamoyloxyethyl) oxocarboxamide, wherein the (R) enantiomer predominates.

2. The compound of claim 1 wherein said (R) enantiomer is present in an amount of about 90% or greater.

3. The compound of claim 1 wherein said (R) enantiomer is present in an amount of about 98% or greater.

4. A compound comprising pure enantiomeric forms, as well as enantiomeric mixtures, of (2-(2-chlorophenyl)-2-carbamoyloxyethyl) oxocarboxamide, wherein the (S) enantiomer predominates.

5. The compound of claim 4 wherein said (S) enantiomer is present in an amount of about 90% or greater.

6. The compound of claim 4 wherein said (S) enantiomer is present in an amount of about 98% or greater.

7. A pharmaceutical composition for treating disorders of the central nervous system which comprises as an active ingredient an effective amount for treating disorders of the central nervous system of a compound as defined in claim 1 and a pharmaceutically acceptable carrier.

8. A pharmaceutical composition for treating disorders of the central nervous system which comprises as an active ingredient an effective amount for treating disorders of the central nervous system of a compound as defined in claim 2 and a pharmaceutically acceptable carrier.

9. A pharmaceutical composition for treating disorders of the central nervous system which comprises as an active ingredient an effective amount for treating disorders of the central nervous system of a compound as defined in claim 3 and a pharmaceutically acceptable carrier.

10. A pharmaceutical composition for treating disorders of the central nervous system which comprises as an active ingredient an effective amount for treating disorders of the central nervous system of a compound as defined in claim 4 and a pharmaceutically acceptable carrier.

11. A pharmaceutical composition for treating disorders of the central nervous system which comprises as an active ingredient an effective amount for treating disorders of the central nervous system of a compound as defined in claim 5 and a pharmaceutically acceptable carrier.

12. A pharmaceutical composition for treating disorders of the central nervous system which comprises as an active ingredient an effective amount for treating disorders of the central nervous system of a compound as defined in claim 6 and a pharmaceutically acceptable carrier.

13. A compound comprising an optically pure enantiomeric form or an enantiomeric mixture of the compound represented by structural formula (II):

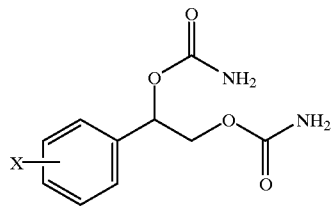

wherein x is a halogen atom substituted on the phenyl ring.

14. The compound of claim 13, wherein the halogen atom is selected from the group consisting of chlorine and fluorine.

15. The compound of claim 13, wherein the halogen atom is substituted at the ortho position of the phenyl ring.

16. The compound of claim 13, wherein the halogen atom is chlorine, and is substituted at the ortho position of the phenyl ring.

17. A pharmaceutical composition for treating disorders of the central nervous system which comprises a pharmaceutically effective amount of a compound of claim 13 and a pharmaceutically acceptable carrier thereof.

* * * * *